United States Patent [19]

Blair

[11] Patent Number: 4,951,685
[45] Date of Patent: Aug. 28, 1990

[54] BLOOD DRAWING SYSTEM

[76] Inventor: Paul A. Blair, 3621 NW. 23 St., Lauderdale Lakes, Fla. 33311

[21] Appl. No.: 193,059

[22] Filed: May 12, 1988

[51] Int. Cl.⁵ ............................................. B65D 85/24
[52] U.S. Cl. .................................... 128/760; 206/365; 206/562; 232/43.3
[58] Field of Search ................................ 206/569-572, 206/363-370, 438, 557-565, 567; 604/110; 128/760; 433/77, 79; 221/263, 264, 268, 270, 208; 232/43.1.43.2, 43.3

[56] References Cited

U.S. PATENT DOCUMENTS

| | | | |
|---|---|---|---|
| 1,116,310 | 11/1914 | Maser | 206/572 |
| 1,554,660 | 9/1925 | Ruskay | 232/43.2 |
| 2,013,281 | 9/1935 | McCalla | 206/572 |
| 2,790,547 | 4/1937 | Sutton | 206/363 |
| 2,985,285 | 5/1961 | Riddle | 206/366 |
| 4,085,845 | 4/1978 | Perfect | 206/363 |
| 4,106,620 | 8/1978 | Brimmer | 206/363 |
| 4,576,281 | 3/1986 | Kirksey | 206/366 |
| 4,736,844 | 4/1988 | Scott et al. | 207/370 |
| 4,801,013 | 1/1989 | Bruno | 206/366 |

Primary Examiner—Stephen C. Pellegrino
Assistant Examiner—Ralph Lewis
Attorney, Agent, or Firm—Alvin S. Blum

[57] ABSTRACT

A system for use with evacuated, rubber stoppered sample tubes and double-ended needles facilitates blood collecting operations and prevents accidental punctures from contaminated needles after use. The tube is held in a tubular cartridge with a sliding control for to and fro controlled motion. A holder engages the mid portion of the needle and the cartridge and the sliding control slides the tube onto the needle after blood vessel puncture and slides it off the needle after collection. A finger control releases the needle while avoiding exposure to the point. A refined receptacle in a phebotomy tray holds used needles and dumps them in controlled fashion without overturning the tray.

1 Claim, 5 Drawing Sheets

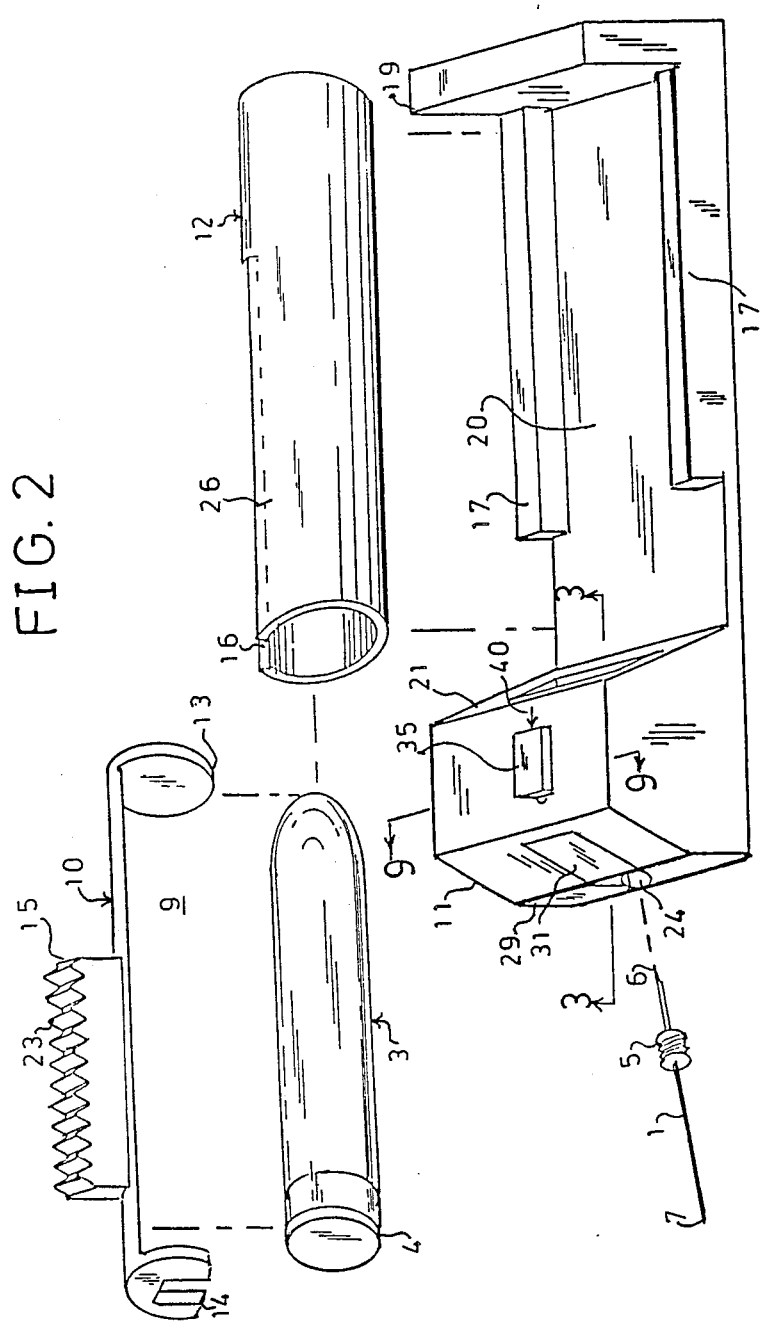

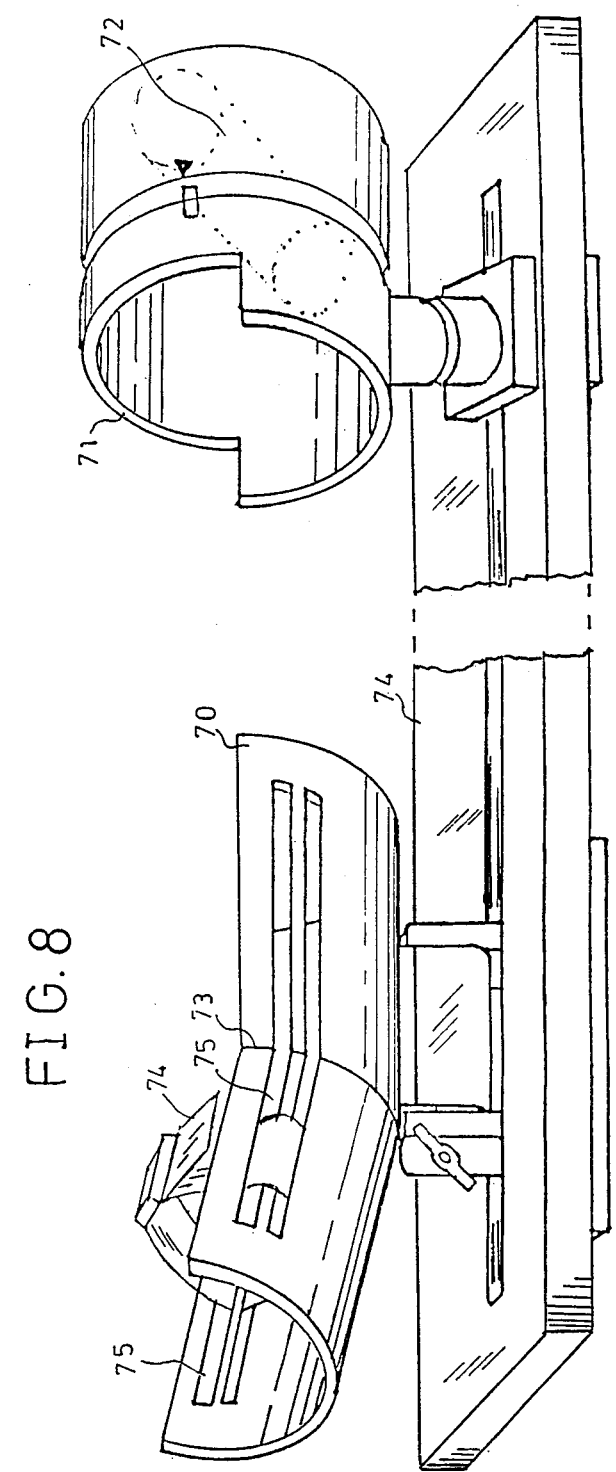

BLOOD DRAWING SYSTEM

BACKGROUND OF THE INVENTION

This invention relates to apparatus for withdrawing blood from veins and more particularly to accessories to be employed with evacuated tubes and double-ended needles to enhance their operation and safety.

To withdraw blood for clinical analysis, a hollow needle sealed to a syringe is used to puncture the skin and an underlying vein or artery. The plunger of the syringe is slowly withdrawn as the blood fills the evacuated space between the plunger and the barrel of the syringe.

The blood is then inserted into one or more sample tubes, which may contain any of a variety of preparations to further the particular analytical procedure, including anticoagulants, preservatives and the like.

An improvement over the syringe that is in wide general use is the evacuated glass tube sealed by a rubber stopper as illustrated in FIG. 1. A double-ended needle 1 is threadably engaged by threads 5 to needle holder 2. The glass tube 3, which may contain any of the preparations to enhance the analysis, contains a vacuum and is sealed by rubber stopper 4. It is inserted into needle holder 2 until the first point 6 of the needle engages, but does not fully penetrate, the rubber stopper 4. The second needle point 7 is then forced through the skin into the blood vessel. The glass tube 3 is then pushed further into needle holder 2 so that it penetrates the stopper and applies the vacuum to the point 7 inside the blood vessel, aspirating blood into the tube. The tube 3 may be withdrawn from the holder 2 and one or more additional tubes may be used to collect additional samples for additional analyses that may require different chemicals within the tube. Care must be exercised in inserting and removing tubes while the needle is in the blood vessel so that the position of needle point 7 is not disturbed by forcing it through the other wall of the vessel or removing it from the vessel or moving it laterally as it may be dislodged from its effective position or may damage the blood vessel.

When sampling is completed, the needle point 7 is removed from the arm, a covering sheath, supplied with the needle is reapplied to the point 7 and the needle is unscrewed from the needle holder 2 and discarded. Alternatively, the needle 1 and needle holder 2 are permanently joined together and are both disposed after a single use. The needle point of the disposable needle holder must also be sheathed prior to discard because of the dangers to users from accidental skin puncture from a needle contaminated with the blood of a person who may be infected with an infectious disease that is transmitted by just such as mechanism.

SUMMARY OF THE INVENTION

It is accordingly an object of the invention to provide an improved system for withdrawing blood samples with evacuated tubes and double-ended needles that reduces the risks of accidental puncture from contaminated needles. It is yet another object of the invention to provide a system that facilitates the process of inserting and removing the tubes. It is yet another object of the invention to provide means to immobilize the arm during the process. It is yet another object to provide means for enhancing the use of the apparatus for sampling from an intravenous tubing assembly.

The assembly of the invention includes: a holder for a needle and cartridge; a cartridge for containing both the evacuated tube and a tube slider; and a tube slider for moving the tube toward and away from the needle in a controlled manner. The invention further includes an immobilizer for holding the arm during phlebotomy, and an adapter for an intravenous tubing diaphragm for use with the assembly, and a safe needle waste receptacle on a phlebotomy tray. These and other objects, advantages, structures and the manner through which the desired results are obtained will be best understood by reference to the accompanying drawings and detailed description.

BRIEF DESCRIPTION OF THE DRAWINGS

FIG. 2 is an exploded perspective view of the blood drawing assembly of the invention.

FIG. 8 is a perspective view of an arm immobilizer for enhancing operation of the blood drawing assembly.

DETAILED DESCRIPTION OF PREFERRED EMBODIMENTS

Figure 9:
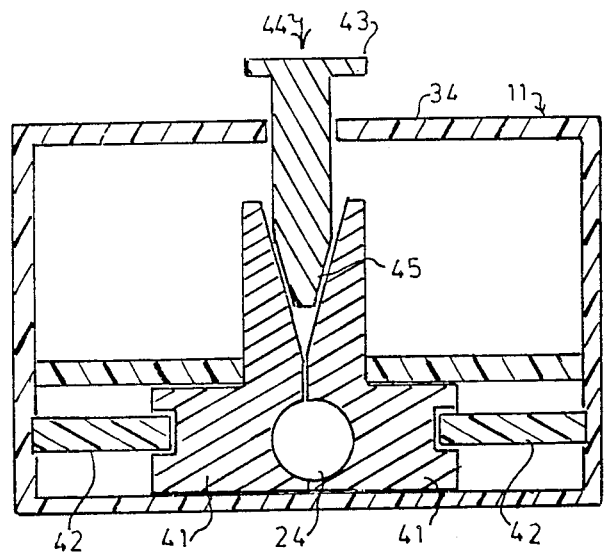
FIG. 9 is a sectional view through 9—9 of FIG. 2 showing an alternative needle-engaging mechanism.
Figure 1:
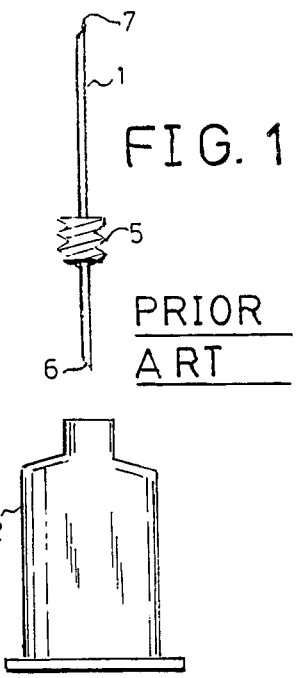
FIG. 1 is a front elevation view of the evacuated tube blood drawing assembly of the prior art.

Referring now first to FIGS. 2, 3, 4, and 5, the evacuated tube 3 is inserted into the space 9 of tube slider 10, between the push end 13 and the pull end 14. The loaded tube slider 10 is then inserted into cartridge 12 with projection 15 on slider 10 passing through slot 16 on upper surface of cartridge 12. The loaded cartridge 12 is then inserted into holder 11. The side elevations 17 and rear elevation 19 are at right angles to the base 20 of holder 11. The front elevation 21 meets base 20 at a sloping angle corresponding to the sloping angle of the front end 22 of cartridge 21 so that the cartridge 12 cannot be inserted incorrectly into the holder and so that it is held snugly in holder 11 during the phlebotomy or blood drawing process.

Figure 5:
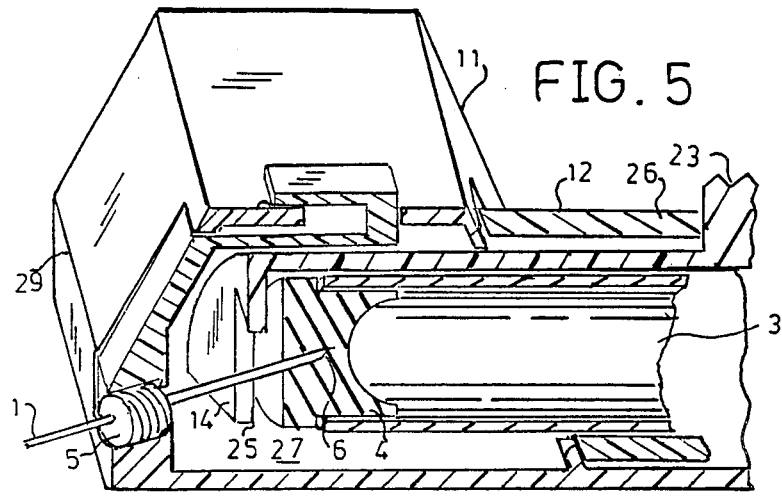
FIG. 5 is a view as in FIG. 3 with the cartridge and needle in place.

Projection 15 on slider 10 has serrations 23 on its upper surface for engaging the finger of the operator to slide the slider 10 and its tube 3 to and fro within the cartridge 12 in place on holder 11. A double-ended needle 1 is removably engaged in aperture 24 of holder 11 by threaded portion 5 as best seen in FIG. 5. As tube 3 is pushed forward, its rubber stopper 4 is impaled by the first point 6 of needle 1 which passes through slot 25 of puller 14 on slider 10. The needle point 6 has not yet penetrated the evacuated space of tube 3, yet it is sealed off by the rubber stopper. This is the preferred condition for initiating the insertion of the needle through the skin and into the blood vessel. If the needle point is not sealed off by the rubber, blood will pass out of the neddle point and around the outside of the tube. If the needle point enters the evacuated space before puncturing the skin, air will enter the tube and, since it has no means of escape, will occupy space that cannot be filled with blood. The invention provides better control over establishing this condition of partial puncture, including an index marker 26 on cartridge 12 to indicate when projection 15 on slider 10 has advanced the tube 13 to that extent inside the chamber 27 at the front end of holder 11. After the needle point 7 has penetrated the skin, the slider 10 is pushed all the way forward, causing needle point 6 to enter the evacuated space. After blood is collected, the slider 10 is moved in the opposite direction, causing its pulling end 14 to pull the stopper off the needle and fully within the cartridge 12. The cartridge 12 may then be removed and replaced with another cartridge if another sample is to be collected before the needle is withdrawn from the patient.

An important aspect of the invention is the means by which the needle 1 is held in holder 11 during phlebotomy and the means whereby the contaminated needle is subsequently removed without exposing the operator to the hazards of accidental puncture. Three alternative embodiments are shown, the first in FIGS. 2–5. The threaded portion 5 of needle 1 is engaged by aperture 24 at the front end 29 of holder 11. This aperture may have smooth walls as shown or may have a female thread matching the threads 5 on needle 1. A ridge 30 at the rear of aperture 24 limits penetration of the needle. The aperture 24 is defined by a lower half that is part of the fixed body of the holder 11 and an upper half that is part of a sliding member 31 that slides rectilinearly in slot 32 at front 29 of holder 11 and slot 33 at top 34 of holder 11. Sliding member 31 extends up above top 34 of holder 11 at finger projection 35. In the position shown, finger projection 35 has been moved fully to the rear in direction of arrow 36 in slot 33 to the needle locked position. The two halves of aperture 24 have a sloping interface 37 that provides a wedge effect pulling both halves together tightly around the threaded portion 5 of needle 1 and holding it securely in place. A small, rounded elevation 39 acts as a detent against the underside of the finger projection 35 which is springy, causing the sliding member to be locked in this position, to release the needle for disposal after use, the finger projection is forced forward in the direction of arrow 40, whereupon the projection 35 springs up over detent 39, the wedge at aperture 24 opens up as sliding member 32 moves forward out of slot 32 in the front face 29 of holder 11. An alternative needle holding mechanism is shown in FIG. 9. The needle holding aperture 24 is defined by two sliding members 41 which are pushed together in the closed position shown by spring elements 42. These spring elements are polyurethane rods. When pushbutton 43 in top 34 of holder 11 is pushed downward as indicated by arrow 44 it spreads apart the sliding members 41 by inclined plane action of its lower wedge portion 45, opening up the orifice 24 to release the needle held therein.

Figure 10:
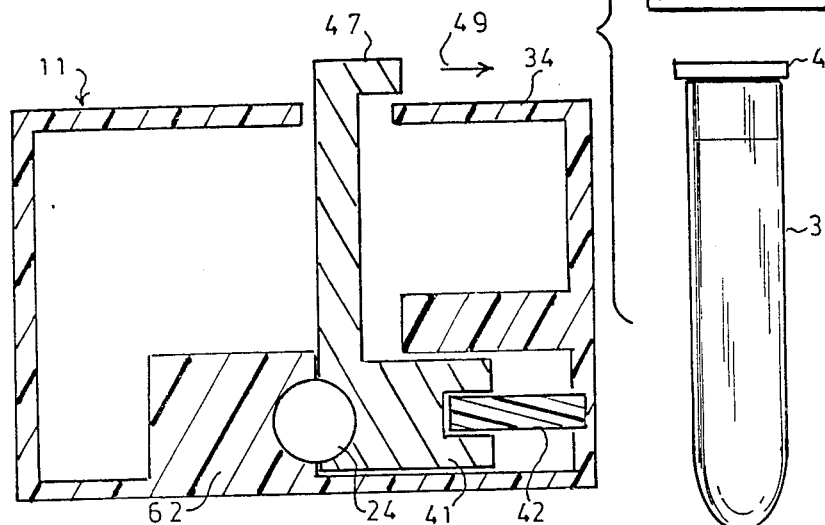
FIG. 10 is a sectional view through 9—9 of FIG. 2 showing yet another alternative needle-engaging mechanism.
Figure 3:
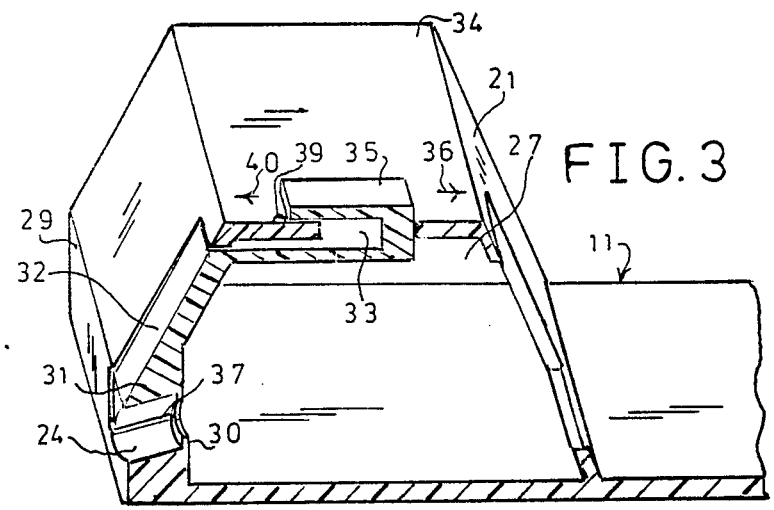
FIG. 3 is a partial sectional view through 3—3 of FIG. 2.
Figure 4:
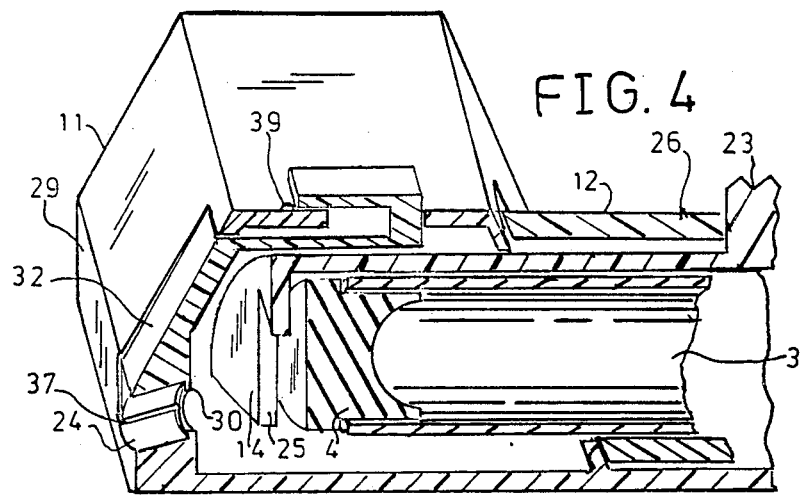
FIG. 4 is a view as in FIG. 3 with the cartridge in place.

In the alternative embodiment of a needle holding mechanism illustrated in FIG. 10, the sliding member 41 forms one half of needle holding aperture 24 and the other half is formed by a fixed member 46 that is fixed to holder 11. Spring element 42 holds the aperture 24 closed. Slide control 47 in top 34 of holder 11 is forced laterally in the direction shown by arrow 49 to slide member 41 laterally, opening up aperture 24 to release the needle. In all three embodiments the needle is released by a control that can be operated without getting the hands near the contaminated needle point.

As best seen in FIGS. 2 and 5, the needle 1 slopes downward from its engagement with the holder 11 to provide a more convenient angle for skin puncture.

Figure 6:
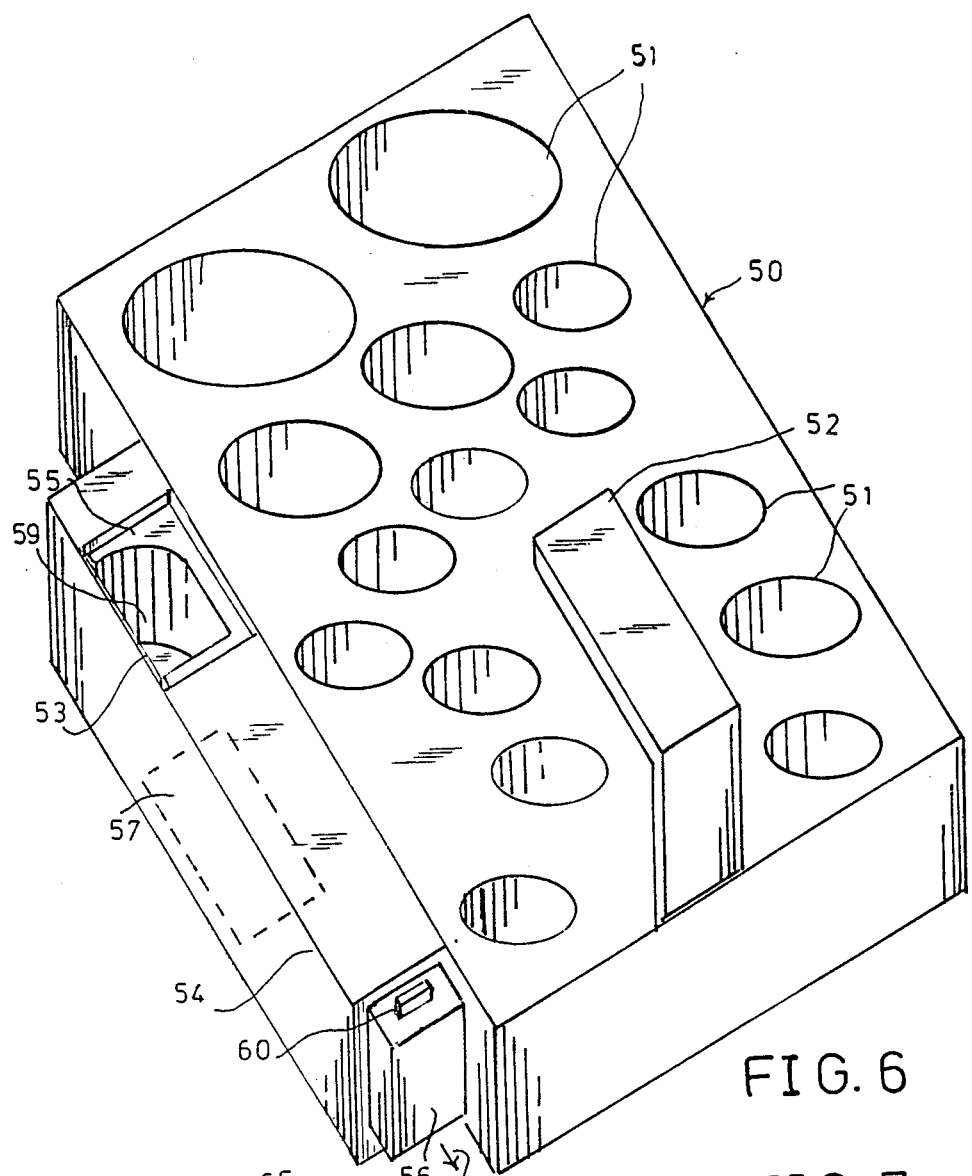
FIG. 6 is a perspective view of the phlebotomy tray with needle waste receptacle.

Referring now to FIG. 6, a blood collecting tray 50 that may be carried to the patient for holding the various necessary supplies including phlebotony accessories in recesses 51 is illustrated. It has carrying handle 52 and a contaminated needle receptacle 53, including a rectangular outer channel 54 with a rectangular aperture 55 in its upper surface, and a rectangular aperture 57 in its lower surface displaced from the upper aperture. A rectangular rod 56 fits slidably within the rectangular channel and slides to and fro by finger control 60 attached thereto. A vertical hole 59 in rectangular rod 56 is positioned beneath upper aperture 55 as shown in the normal operating position of inner rod 56, wherein the combination provides a receptacle for holding contaminated needles which may be dropped directly from the holder 11 when needle is released from the needle holding mechanism without touching the needle directly. When the operater wishes to empty the contaminated needles from the receptacle 53, the tray is held over the waste container with rectangular opening 57 in the bottom of channel 54 directly over the opening in the waste container. Finger control 60 pulls rod 56 in the direction of arrow 61 until the vertical aperture 59 in rod 56 is directly over aperture 57 in lower surface of channel 54, whereupon the needles stored therein drop down through the aperture and into the waste container. This avoids problems with tilting the tray without dumping the other items stored therein.

Figure 7:
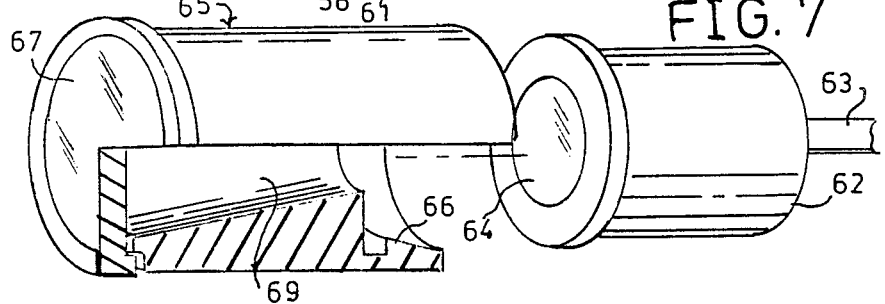
FIG. 7 is a perspective view of a needle puncture diaphragm on an intravenous tube together with an adapter therefor for enhancing operation of the blood drawing assembly for intravenous tube application.

FIG. 7 shows an injector element 62 of the prior art as it is normally connected to an intravenous tubing 63 for the injection of medication through rubber diaphragm 64. To facilitate the use of the blood sampling invention with the injector element 62 an adapter 65 is provided that snaps onto the injector element 62 with resilient tapered element 66. The adapter 65 provides a larger rubber diaphragm 67 that is an easier target for the needle. The tapered chamber 69 beyond the diaphragm 67 provides a funnel mechanism to direct the needle into the smaller diaphragm 64.

FIG. 8 shows an arm rest 70 to immobilize the arm and hold a tourniquet while drawing blood with the blood drawing device of the invention. The hand fits within the cylindrical element 71 and grips the handle bar 72 shown in phantom which is freely rotatable within element 71. The elbow will fit into the angle 73 and tourniquet 74, held captive in slots 75 is removably applied to the arm as required. The elements 70 and 71 are slidably mounted on base 74 to adjust to various size arms.

The above disclosed invention has a number of particular features which should preferably be employed in combination although each is useful separately without departure from the scope of the invention. While I have shown and described the preferred embodiments of my invention, it will be understood that the invention may be embodied otherwise than as herein specifically illustrated or described, and that certain changes in the form and arrangement of parts and the specific manner of practicing the invention may be made within the underlying idea or principles of the invention within the scope of the appended claims.

I claim:

1. A phlebotomy tray means for carrying phlebotomy accessories including a plurality of recesses in a top surface of said tray for receiving said phlebotomy accessories and a contaminated needle receptacle for intermediate storage of contaminated needles, said needle receptacle including: an elongate sliding inner member having a vertical hole therethrough; and an elongate outer member connected to said tray, said outer member having an elongate inner channel closely fitting said inner member so that said inner member slides within said channel, a top opening in the upper surface of said outer member and a bottom opening in the lower surface of said outer member, wherein said openings are so arranged relative to said vertical hole in said inner member that said top opening and vertical hole combine to form a receptacle with a closed bottom for holding said needles in a first position of said sliding inner member and said bottom opening and said vertical hole provide a receptacle with a closed top and an open bottom in a second position of said sliding inner member, whereby needles stored in said receptacle are free to fall from said tray and are thereby removed from said tray without overturning said tray.

* * * * *